US006403645B2

(12) United States Patent
Schildkraut et al.

(10) Patent No.: US 6,403,645 B2
(45) Date of Patent: Jun. 11, 2002

(54) ANTIDEPRESSANT EFFECT OF NOREPINEPHRINE UPTAKE 2 INHIBITORS AND COMBINED MEDICATIONS INCLUDING THEM

(75) Inventors: Joseph J. Schildkraut, Chestnut Hill; John J. Mooney, Belmont, both of MA (US)

(73) Assignee: President and Fellows of Harvard College, MA (US)

( * ) Notice: Subject to any disclaimer, the term of this patent is extended or adjusted under 35 U.S.C. 154(b) by 0 days.

(21) Appl. No.: 09/811,235

(22) Filed: Mar. 16, 2001

Related U.S. Application Data

(60) Provisional application No. 60/189,828, filed on Mar. 16, 2000.

(51) Int. Cl.$^7$ .................. A61K 31/195; A61K 31/55; A61K 31/53; A61K 31/335; A61K 31/135

(52) U.S. Cl. .................. 514/567; 514/211; 514/217; 514/242; 514/450; 514/653; 514/654

(58) Field of Search .................. 514/567, 653, 514/217, 654, 211, 450, 242

(56) References Cited

U.S. PATENT DOCUMENTS

| | | |
|---|---|---|
| 3,723,514 A | 3/1973 | Hegedus et al. |
| 4,480,109 A | 10/1984 | Ohashi et al. |
| 4,562,263 A | 12/1985 | Ohashi et al. |
| 5,266,596 A | 11/1993 | Yokokawa et al. |
| 5,288,898 A | 2/1994 | Umezawa et al. |
| 5,739,387 A | 4/1998 | Oda et al. |
| 5,864,041 A | 1/1999 | Oda et al. |

OTHER PUBLICATIONS

Abstract from EP–112606–A (Jul. 1984).
Abstract from J59199660 (Nov. 1984).
Abstract from EP–528729–A+(Feb.1993).
Abstract from EP–576941–A+(Jan. 1994).
Bartholini et al., "The Stereoisomers of 3, 4–Dihydroxyphenylserine as Precursors of Norepinephrine", *The Journal of Pharmacology and Experimental Therapeutics*, vol. 193, No. 3, pp. 523–532, (1974).
Bolden–Watson et al., "Blockade by Newly–Developed Antidepressants of Biogenic Amine Uptake into Rat Brain Synaptosomes", *Life Sciences*, vol. 52, pp. 1023–1029, (Jan. 1993).
Creveling et al., "The Combined Use of a–Methyltryosine and Threo–Dihydroxyphenylserine–Selective Reduction of Dopamine Levels in the Central Nervous System", *Biochemical Pharmacology*, vol. 17, pp. 65–70, Pergamon Press, (1968).
Grundemann et al., "Molecular identification of the corticosterone–sentsitive extraneuronal catecholamine transporter", *Nature Neuroscience*, vol. 1, No. 5, (Sep. 1998).

Hendley, "The Mechanism of Extraneuronal Transport of Catecholamines in the Central Nervous System", The Mechanism of Neuronal and Extraneuronal Transport of Catecholamines, Raven press, New York (1976).
Inagaki et al., "Inhibitory Effect of (+)Threo–3, 4–Dihydroxyphenylserine (DOPS) on Decarboxylation of (–)Threo–DOPS", *Japan. J. Pharmacol.*, vol. 26, pp. 380–382, (1976).
Kato et al., "Studies on the Activity of $_L$–Threo–3,4–Dihydroxyphenylserine ($_L$–DOPS) as a Catecholamine Precursor in the Brain", *Biochemical Pharmacology*, vol. 36, No. 18, pp. 3051–3057. (1967).
Katsube et al., "Development of L–threo–DOPS, a Norepinephrine Precursor Amine Acid", *Yakugaku Zasshi*, vol. 144, No. 11, pp. 823–846, (1994).
Martel et al., "Comparison between uptake$_2$ nd rOCT1: effects of catecholamides, metanephrines and corticosterone", *Naunyn–Schmiedeberg's Arch Pharmacol*, vol. 359, pp. 303–309, (1999).
Maruyama et al., "A new metabolic pathway of $_L$–threo–3, 4–dihydroxyphenylserine, a precursor amino acid of norepinephrine, in the Studies by in vivo microdialysis", *J. Neural Transm.*, vol. 7, pp. 21–33, (1994).
Maruyama et al., "The metabolism of $_L$–DOPA and $_L$–Threo–3, 4–dihydroxyphenylserine and their effects on monoamines in the human brain: analysis of the intraventricular fluid from parkinsonian patients", *Journal of the Neurological Sciences*, vol. 139, pp. 141–148, (1996).
Naoi et al., "L–Threo–3, 4–Dihydroxyphenylserine (DOPS) Aldolase: A New Enzyme Cleaving DOPS Into Protocatechualdehyde and Glycine", *Biochemical and Biophysical Research Communications*, vol. 143, No. 2, pp. 482–488, (Mar. 1987).

(List continued on next page.)

*Primary Examiner*—William R. A. Jarvis
(74) *Attorney, Agent, or Firm*—Fish & Richardson P.C.

(57) ABSTRACT

Norepinephrine uptake 2 inhibitors (or their precursors) are administered to enhance the effect of norepinephrine reuptake inhibitors and other antidepressants. The uptake 2 inhibitor may be combined in a single medication with a norepinephrine reuptake inhibitor, such as imipramine, desipramine, or reboxetine, in order to inhibit both uptake mechanisms. The norepinephrine uptake 2 inhibitors may also be combined with MAO inhibitors or with selective serotonin reuptake inhibitors. Alternatively, the norepinephrine uptake 2 inhibitors may be useful antidepressants in their own right, without the need for co-administration of other antidepressants. One class of norepinephrine uptake 2 inhibitors is normetanephrine (the O-methylated metabolite of norepinephrine) and normetanephrine precursors [such as 3(4-hydroxy-3-methoxyphenyl)-serine (4H-3MePS ), particularly L-threo-3-(4-H-3 MePS)] that are transported to the brain where they are converted into normetanephrine, thereby enhancing the effect of other antidepressants. For example, the invention enhances the antidepressant effect of norepinephrine reuptake inhibitors.

32 Claims, 1 Drawing Sheet

OTHER PUBLICATIONS

Porter et al., "(S)–Norepinephrine * in the Tissues of Mice and Rats Given Racemic Erythro–3, 4–Dihydroxyphenylserine (DOPS)", *Life Sciences,* vol. 11, Part I, pp. 787–795, (1972).

Russ et al., "The extaneuronal transport mechanism for noradrenaline (uptake$_2$) avidly transports 1–methyl–4–phenylpyridinium (MPP$^+$)*", *Naunyn –Schmiedeberg's Arch Pharmacol,* vol. 346, pp. 158–165, (1992).

Russ, et al., "The Extraneuronal Transporter for Monoamine Transmitters Exists in Cells Derived from Human Central Nervous System Glia", *European Journal of Neuroscience,* vol. 8, pp. 1256–1264, (1996).

Schildkraut et al., "Normetanephrine Excretion and Affective State in Depressed Patients Treated with Imipramine", *Amer. J. Psychiat,* vol. 123, pp. 690–700, (Oct. 1966).

Streich et al., "Expression of the extraneuronal monoamine transporter (uptake$_2$) in human glioma cells", *Naunyn –Schmiedeberg's Arch Pharmacol,* vol. 353, pp. 328–333, (1996).

Yamamoto et al., "Effect of $_L$–Threo–3, 4–dihydroxyphenylserine Chronic Administration on Cerebrospinal Fluid and Plasma Free 3–Methoxy–4–hydroxy–phenylglycol Concentration in Patients with Parkinson's Disease", *Journal of Neurological Sciences,* vol. 73, pp. 39–44, (1986).

Maruyama et al, Clinical Neurology, No. 34, 985–990, 1994.

ANTIDEPRESSANT EFFECT OF NOREPINEPHRINE UPTAKE 2 INHIBITORS AND COMBINED MEDICATIONS INCLUDING THEM

This application claims priority to provisional application No. 60/189,828, filed Mar. 16, 2000.

TECHNICAL FIELD

This invention is in the general field of central nervous system medications, particularly antidepressants.

BACKGROUND

Norepinephrine is released from presynaptic noradrenergic neurons into the synapse. One therapy for clinical depression is administration of drugs known as norepinephrine reuptake inhibitors, such as imipramine, desipramine, or reboxetine, which inhibit the reuptake of norepinephrine into the presynaptic neuron ("uptake 1"), the main mechanism of inactivating norepinephrine at the synapse. Reuptake inhibition thus increases synaptic norepinephrine levels. [Bolden-Watson and Richelson, *Life Sciences*, 52:1023–1029 (1993), hereby incorporated by reference, discloses a method for determining reuptake inhibition.] Typically these drugs are administered chronically and there may be a significant delay, e.g. 4–6 weeks, between the onset of therapy and clinical improvement.

Other therapies feature the administration of other classes of drugs, such as monoamine oxidase (MAO) inhibitors or selective serotonin reuptake inhibitors.

In a study of depressed patients treated with the antidepressant imipramine, there was a gradual increase in urinary levels of normetanephrine, the O-methylated metabolite of norepinephrine, during the period of definitive clinical improvement from depression—Schildkraut et al., *American Journal of Psychiatry*, 123:690–700 (1966).

SUMMARY

Norepinephrine present in the synapse or other extraneuronal spaces can also be taken up into glia and other cells by a mechanism known as uptake 2 or extraneuronal uptake. In glia (and other cells), such norepinephrine may be converted to its O-methylated metabolite, normetanephrine, which is an inhibitor of uptake 2. Administration of compounds that lead to an increase in brain levels of norepinephrine uptake 2 inhibitors will enhance the antidepressant effect of norepinephrine reuptake inhibitors. Accordingly, one aspect of the invention features co-administration and co-formulation of a compound that inhibits norepinephrine uptake 2 (or a precursor thereof) together with another antidepressant compound, particularly a norepinephrine reuptake inhibitor (acting at uptake 1). The uptake 2 inhibitor or precursor may be normetanephrine or a normetanephrine precursor that crosses the blood-brain barrier where it is converted to normetanephrine, the latter being a norepinephrine uptake 2 inhibitor that increases the level of extraneuronal norepinephrine in the brain. The effect of other antidepressants should also be enhanced by the use of norepinephrine uptake 2 inhibitors. Among the other antidepressants to be evaluated are MAO inhibitors and selective serotonin reuptake inhibitors.

In clinical studies of depressed patients treated with the norepinephrine reuptake inhibitor antidepressant desipramine, we have found that after one week of treatment, there were small decreases in urinary levels of norepinephrine and normetanephrine. However, by the fourth week of treatment with desipramine, urinary levels of norepinephrine and normetanephrine showed statistically significant increases, and these increases were even more pronounced and statistically significant after six weeks of treatment with desipramine. Similar findings were observed in studies of levels of norepinephrine in plasma during treatment with desipramine in these patients. (Plasma levels of normetanephrine were not measured in these studies.)

Without wishing to bind ourselves to a specific molecular mechanism to the exclusion of other mechanisms, various substances such as normetanephrine block uptake of norepinephrine via uptake 2. Moreover, such uptake 2 inhibitors complement norepinephrine uptake 1 inhibitors, in that each works independently to enhance extraneuronal norepinephrine levels in the brain. The invention therefore further increases levels of norepinephrine present at the synapse and surrounding extraneuronal spaces, thereby providing a more rapid antidepressant effect for norepinephrine reuptake inhibitors.

Again, without wishing to bind ourselves exclusively to a mechanism of action, we note the following regarding the invention's ability to reduce the time required for clinical antidepressant effects from the administration of norepinephrine reuptake inhibitors. Reuptake inhibition at uptake 1 sites initially results in an increase of norepinephrine at the synapse. This results in the activation of presynaptic $alpha_2$-adrenergic receptors as well as somatodendritic $alpha_2$-adrenergic receptors on noradrenergic neuronal cell bodies in the locus coeruleus (the nucleus containing norepinephrine cell bodies in the brain), and the consequent feedback inhibition of locus coeruleus firing rates and norepinephrine release from presynaptic noradrenergic neurons. Over time, the continued presence of norepinephrine in the synapse produces a decrease in the sensitivity of these $alpha_2$-adrenergic receptors, and this decrease in the sensitivity of presynaptic and somatodendritic $alpha_2$-adrenergic receptors contributes to an increase of locus coeruleus firing rates and an increased release of norepinephrine from presynaptic neurons—Linner et al., *Biological Psychiatry* 46: 766–774 (1999); Schildkraut et al., *Science*, 168:867–869 (1970)—further enhancing synaptic levels of norepinephrine during long-term administration of norepinephrine reuptake inhibitor drugs and enhancing clinical antidepressant effects. By directly inhibiting norepinephrine uptake 2, the invention will further enhance the accumulation of norepinephrine in the synapse and extraneuronal spaces and should reduce the time required for clinical improvement during the administration of norepinephrine reuptake (uptake 1) inhibitors. Moreover administration of an $alpha_2$-adrenergic receptor antagonist (e.g. idazoxan) in conjunction with a norepinephrine uptake 2 inhibitor (with or without a norepinephrine reuptake (uptake 1) inhibitor) would further enhance the accumulation of norepinephrine in the synapse and extraneuronal spaces.

Normetanephrine also may be a biological $alpha_2$-adrenoreceptor antagonist—Lenz et al., *Canadian Journal of Physiology and Pharmacology* 69: 929–937 (1991)—and, as an $alpha_2$-adrenergic receptor antagonist, normetanephrine may increase both locus coeruleus firing rates and the rate of release of norepinephrine from presynaptic neurons. Thus, normetanephrine may contribute to clinical antidepressant effects by pharmacological mechanisms in addition to or other than blocking uptake 2.

Uptake 2 inhibitors or precursors that are particularly useful are those that cross the blood/brain barrier where they are converted to normetanephrine, the latter being a compound that acts to inhibit uptake 2. Specific normetanephrine precursors that are useful according to the invention include those metabolized via a pathway that includes the conversion of L-threo-3-(4-hydroxy-3-methoxyphenyl)-serine ("L-threo-4H-3MePS") into normetanephrine by an L-aromatic amino acid decarboxylase present in the brain. In one detailed embodiment, the invention features the use of 4H-3MePS itself (particularly L-threo-4H-3MePS).

The invention can be used in conjunction with compounds blocking peripheral decarboxylation of 4H-3MePS (such as carbidopa), a process that would otherwise convert some 4H-3MePS into normetanephrine, which is less able to cross the blood/brain barrier. Preferably, the norepinephrine reuptake inhibitor component of the combination is imipramine, desipramine, or reboxetine. Other norepinephrine reuptake inhibitors that can be used include nortriptyline, maprotiline, protriptyline, trimipramine, and venlafaxine. Still other candidates include amitriptyline, amoxapine, doxepin, nefazodone, and lamotrigine.

Advantageously, the norepinephrine uptake 2 inhibitor and the second antidepressant are formulated in a single medicament.

A second aspect of the invention features administering an uptake 2 inhibitor (or a precursor thereof, such as L-threo-4H-3MePS), that provides antidepressant effect by itself.

The details of one or more embodiments of the invention are set forth in the detailed description below. Other features, objects, and advantages of the invention will be apparent from the description and drawings, and from the claims.

DETAILED DESCRIPTION

Figure 1:
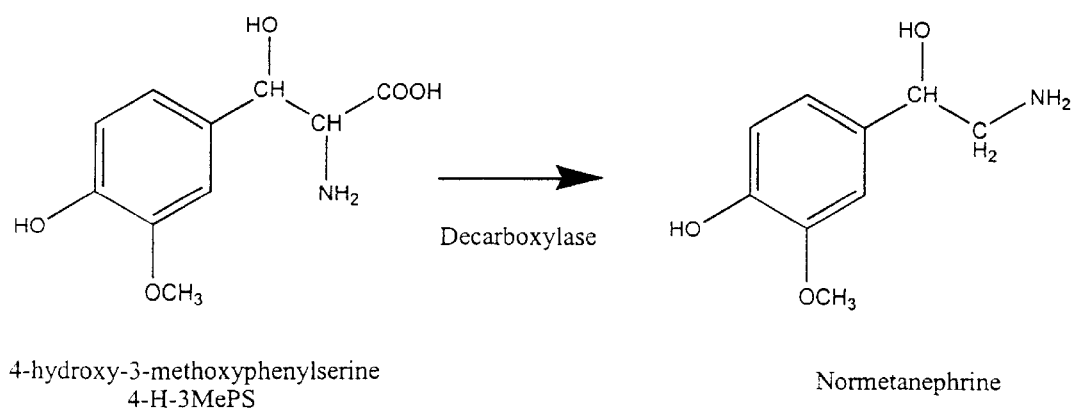
FIG. 1 shows the in vivo conversion of 4H-3MePS to normetanephrine.

I. The Uptake 2 Inhibitor or Precursor Thereof

The uptake 2 inhibitor or precursor thereof can be normetanephrine or normetanephrine metabolic precursors that are metabolized via a pathway concluding with the conversion of L-threo-3-(4-hydroxy-3-methoxyphenyl)-serine ("L-threo-4H-3MePS") into normetanephrine by an L-aromatic amino acid decarboxylase present in the brain. While we do not rule out the possibility that there may be other compounds in the pathway that would be useful in the invention, we have identified 4H-3MePS itself as the preferred precursor compound. The formula of 4H-3MePS and its conversion to normetanephrine are illustrated in FIG. 1.

The compound can be obtained from commercially available starting materials by the general method described in U.S. Pat. No. 3,723,514, which is hereby incorporated by reference. Optically active 4H-3MePS (particularly the L-threo-stereoisomer) may be obtained by reacting a derivative of racemic 4H-3MePS with an optically active base or an optically active acid, as described in the '514 patent.

Those skilled in the art will understand that, in addition to normetanephrine precursors, other uptake 2 inhibitors or precursors could be used. For example, normetanephrine itself, formulated in a way that crosses the blood/brain barrier could be used. Finally, the normetanephrine precursors may be replaced by or co-administered with other uptake 2 inhibitors, such as cortisol, cimetidine, clonidine, quinine, metanephrine, 3-O-methylisoprenaline, amphetamine, phenethylamine, phenoxybenzamine, phentolamine, prazosin.

The ability of a compound to inhibit uptake 2 of norepinephrine can be verified by the general methods described in Russ et al., *Eur. J. Neurosci.* 8:1256–1264 (1996), or Streich et al. *Naunyn-Schmiedeberg's Arch Pharmacol.*, 353:328–333 (1996), each of which is hereby incorporated by reference.

II. Co-administration with Reuptake Inhibitors or Other Antidepressants

As noted, the normetanephrine precursor or other uptake 2 inhibitors or precursors may be combined with norepinephrine reuptake inhibitors, i.e., those that inhibit norepinephrine uptake 1. Specifically, the uptake 2 inhibitor or precursor may be combined with: imipramine, desipramine, or reboxetine. Other norepinephrine reuptake inhibitors are: nortriptyline, maprotiline, protriptyline, trimipramine, and venlafaxine. Still other reuptake inhibitors include: amitriptyline, amoxapine, doxepin, nefazodone, and lamotrigine.

The normetanephrine precursors may also be combined with other antidepressants such as monoamine oxidase inhibitors (phenelzine, tranylcypromine, isocarboxazid, selegiline (L-deprenyl)) or selective serotonin reuptake inhibitors (fluoxetine, sertraline, paroxetine, fluvoxamine, and citalopram). Other compounds that can be evaluated for use in the invention include: stimulants (e.g., amphetamine) or other drugs that presumably have antidepressant effect such as adinazolam, adrafinil, amineptine, befloxatone, brofaromine, bupropion, captopril (capoten), clomipramine, corticotropin-releasing factor (CRF) antagonists, dothiepin (prothiaden), duloxetine, fengabine, flesinoxan, idazoxan, inositol, lofepramine, mianserin (bolvidon, norval), medifoxamine, milnacipran, minaprine, mirtazapine, moclobemide, modafanil, ondansetron (zofran), ProzacII, ritanserine (tisterton), rolipram, roxindole, S-adenosyl-L-methionine (SAMe), substance P antagonists, sulpiride (dogmatil), sunepitron, tianeptine, and trazodone.

III. Administration of the Uptake 2 Inhibitor or Precursor

The compounds to be administered can be formulated into a suitable pharmaceutical preparation by known techniques. For example the '514 patent discloses tablet and capsule formulations. Such formulations typically comprise the active agent (or the agent in a salt form) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include oral, intravenous, intradermal, subcutaneous, transdermal (topical), transmucosal (e.g. intranasal), and rectal.

By far the most convenient route of administration is oral (ingestion). Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating depression by administering to a patient in need of such treatment an antidepressant amount of a norepinephrine uptake 2 inhibitor (or a precursor thereof) in combination with a second antidepressant.

2. The method of claim 1 in which the norepinephrine uptake 2 inhibitor is normetanephrine or a normetanephrine precursor.

3. The method of claim 2, in which the normetanephrine precursor is 4-hydroxy-3-methoxyphenylserine (4H-3MePS). methoxyphenylserine (4H-3MePS ), particularly L-threo-3-(4-H-3MePS).

4. The method of claim 1, in which the second antidepressant is a norepinephrine reuptake inhibitor.

5. The method of claim 4, in which the norepinephrine reuptake inhibitor is imipramine, desipramine or reboxetine.

6. The method of claim 4, in which the norepinephrine reuptake inhibitor is nortriptyline, maprotiline, protriptyline, trimipramine or venlafaxine.

7. The method of claim 4, in which the norepinephrine reuptake inhibitor is amitriptyline, amoxapine, doxepin, nefazodone, or lamotrigine.

8. The method of claim 1, in which the norepinephrine uptake 2 inhibitor and the second antidepressant are formulated in a single medicament.

9. The method of claim 1 in which the norepinephrine uptake 2 inhibitor is co-administered with a selective serotonin reuptake inhibitor.

10. The method of claim 1 in which the norepinephrine uptake 2 inhibitor is co-administered with a monoamine oxidase inhibitor.

11. The method of claim 2 or claim 3 further comprising administration of a peripheral decarboxylase inhibitor.

12. The method of claim 11 in which the peripheral decarboxylase inhibitor is carbidopa.

13. A medicament comprising, in combination, depression-counteracting amounts, of: a) a norepinephrine uptake 2 inhibitor (or a precursor thereof); and b) a second antidepressant compound.

14. The medicament of claim 13 in which the norepinephrine uptake 2 inhibitor is normetanephrine or a normetanephrine precursor.

15. The medicament of claim 14, in which the normetanephrine metabolic precursor is 4-hydroxy-3methoxyphenylserine.

16. The medicament of claim 13, in which the second antidepressant is a norepinephrine reuptake inhibitor.

17. The medicament of claim 16, in which the norepinephrine reuptake inhibitor is imipramine, desipramine or reboxetine.

18. The medicament of claim 16 in which the norepinephrine reuptake inhibitor is nortriptyline, maprotiline, protriptyline, trimipramine or venlafaxine.

19. The medicament of claim 16, in which the norepinephrine reuptake inhibitor is amitriptyline, amoxapine, doxepin, nefazodone, or lamotrigine.

20. The medicament of claim 13, in which the norepinephrine uptake 2 inhibitor and the second antidepressant are formulated in a single medicament.

21. The medicament of claim 13 in which the norepinephrine uptake 2 inhibitor is combined with a selective serotonin reuptake inhibitor.

22. The medicament of claim 13 in which the norepinephrine uptake 2 inhibitor is combined with a monoamine oxidase inhibitor.

23. The medicament of claim 14 or claim 15 further comprising a peripheral decarboxylase inhibitor.

24. The medicament of claim 23 in which the peripheral decarboxylase inhibitor is carbidopa.

25. A method of treating depression by administering to a patient in need of such treatment an antidepressant amount of a norepinephrine uptake 2 inhibitor, or a precursor thereof.

26. A method of making of claim 25 in which the precursor to a norepinephrine uptake 2 inhibitor is 4H-3MePS.

27. The method of claim 26 further comprising administering a peripheral decarboxylase inhibitor.

28. The method of any one of claims 25, 26 or 27 further comprising administration of an alpha$_2$-adrenergic receptor antagonist in conjunction with the norepinephrine uptake 2 inhibitor.

29. The method of claim 28 in which the alpha$_2$-adrenergic receptor antagonist is idazoxan.

30. The method of claim 3 in which said normetanephrine precursion is L-threo-3-(4H-3MePS).

31. The medicament of claim 15 in which the normepinephrine precursor is L-threo-3-(4-H-3MePS).

32. The medicament of claim 26 in which the normepinephrine precursor is L-threo-3-(4-H-3MePS).

* * * * *

UNITED STATES PATENT AND TRADEMARK OFFICE
CERTIFICATE OF CORRECTION

PATENT NO.         : 6,403,645 B2
APPLICATION NO.    : 09/811235
DATED              : June 11, 2002
INVENTOR(S)        : Joseph J. Schildkraut and John J. Mooney It is certified that error appears in the above-identified patent and that said Letters Patent is hereby corrected as shown below:

On the cover sheet, column 2, line 14, delete "Amine" and insert --Amino--.

On the cover sheet, column 2, line 16, delete "nd" and insert --and--.

On page 2, column 2, line 3, delete "(Oct. 1966)" and insert --(Dec. 1966)--.

Signed and Sealed this

Seventh Day of September, 2010

David J. Kappos
*Director of the United States Patent and Trademark Office*